(12) United States Patent
Ribaric et al.

(10) Patent No.: US 8,303,115 B2
(45) Date of Patent: Nov. 6, 2012

(54) METHOD AND SYSTEM FOR RETINAL HEALTH MANAGEMENT

(75) Inventors: Zeljko Ribaric, Ottawa (CA); Robert A. Andrews, Ottawa (CA); Eric Desgroseilliers, Chelsea (CA); Alan Boate, Ottawa (CA); Richard Clayton, Ottawa (CA); Derek C. Thorslund, Ottawa (CA)

(73) Assignee: Annidis Health Systems Corp., Ottawa, Ontario (CA)

( * ) Notice: Subject to any disclaimer, the term of this patent is extended or adjusted under 35 U.S.C. 154(b) by 53 days.

(21) Appl. No.: 12/790,343

(22) Filed: May 28, 2010

(65) Prior Publication Data

US 2010/0302507 A1  Dec. 2, 2010

Related U.S. Application Data

(60) Provisional application No. 61/181,863, filed on May 28, 2009.

(51) Int. Cl.
*A61B 3/14* (2006.01)
*A61B 3/10* (2006.01)
*A61B 3/00* (2006.01)

(52) U.S. Cl. ......... 351/206; 351/205; 351/200; 351/221

(58) Field of Classification Search ........... 351/200–246
See application file for complete search history.

(56) References Cited

U.S. PATENT DOCUMENTS

| 7,222,961 B2 * | 5/2007 | Soliz et al. ..................... 351/200 |
| 7,774,036 B2 * | 8/2010 | Halldorsson et al. ......... 600/323 |
| 2006/0276698 A1 | 12/2006 | Halldorsson |

OTHER PUBLICATIONS

International Application No. PCT/CA2010/000785, Search Report dated Oct. 7, 2010.

* cited by examiner

*Primary Examiner* — Mohammed Hasan
(74) *Attorney, Agent, or Firm* — David Nauman; Borden Ladner Gervais LLP

(57) ABSTRACT

A method for quantifying disease progression through retinal health assessment and management. The method comprises obtaining a first image of a retina or iris at a point in time; generating a first vascular map of the first image of the retina or the iris; obtaining a second image of the retina or the iris at a later point in time; generating a second vascular map of the second image of the retina or the iris; registering the first image and the second image on the basis of the first vascular map and the second vascular map; and displaying at least one difference between the registered first image and the second image to quantify a disease progression.

18 Claims, 15 Drawing Sheets

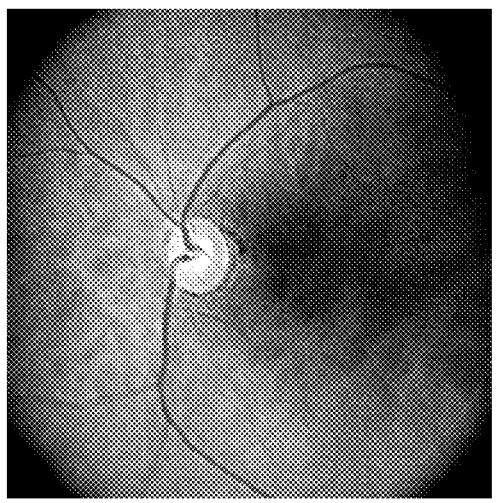
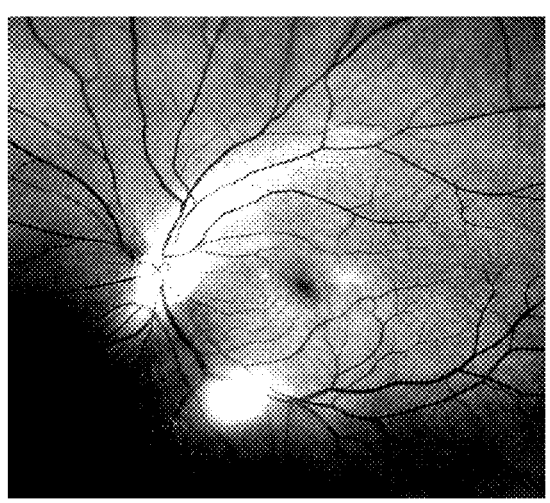
Fig. 3a
Fig. 3b

Clinical Viewer: Layout and Buttons labeled for OD (right) eye, buttons are mirrored for OS (left) eye Clinical Viewer: Tabs and Buttons in Detail Clinical Viewer: Visit Screen Clinical Viewer: Glaucoma Management: Cup to Disc ratio (C/D), IOP, over time tracking and viewing Clinical Viewer: Glaucoma Management: Both Eyes; OD Cup to Disc ratio (C/D), OS Advanced Cup enhancement Image processing Clinical Viewer: Glaucoma Management: Both Eyes; OD Cup to Disc ratio (C/D), OS Retinal Oxygen in Vessels Clinical Viewer: Age Related Macular Degeneration (ARMD): Color Image OD & OS, enhanced pigment and Lipid view Clinical Viewer: Age Related Macular Degeneration (ARMD): OD Eye Geographic Atrophy and Drusen area coverage, and over time tracking Clinical Viewer: Age Related Macular Degeneration (ARMD): OD Eye Geographic Atrophy and OS: Drusen area coverage, and over time tracking Clinical Viewer: Age Related Macular Degeneration (ARMD): OD Eye Relative Oxygen and OD: Hemes, area coverage, and over time tracking Clinical Viewer: Diabetic Retinopathy (DRP): Both Eyes; OD Eye Vessel Map; OS Eye: Hemes, area coverage, and over time tracking

METHOD AND SYSTEM FOR RETINAL HEALTH MANAGEMENT

CROSS REFERENCE TO RELATED APPLICATIONS

This application claims the benefit of priority of U.S. Provisional Patent Application 61/181,863 filed on May 28, 2009, which is incorporated herein in its entirety by reference.

TECHNICAL FIELD

The present application relates generally to retinal health management. More particularly, the present application relates to a method and system for quantifying disease progression through retinal health assessment and management.

BACKGROUND

The power and sophistication of photonic technology lends itself to the advancement of the medical science of opthalmology wherein the photonic technology can be deployed to capture information in a non-invasive manner. Such information typically pertains to the retina.

The human eye can be described as a complex optical and physiological system whose purpose is to provide an image of the environment to the brain. The anatomy of the human eye is shown in FIG. 1. As with any camera, the front portion of the eye (cornea and crystalline lens) acts as a focusing element that produces an image on the back surface of the eye (the retina) where photochemical transducers convert the optical signal into electrical signals that can be understood by the brain.

Direct visual observation of the retina can be used for non-invasive diagnostic purposes. It is, therefore, desirable to provide a method and system for quantifying disease progression through retinal health assessment and management.

SUMMARY

In a first aspect, the present application provides a method for quantifying disease progression through retinal health assessment and management.

In further aspect, the present application provides a system for quantifying disease progression through retinal health assessment and management.

Other aspects and features of the present application will become apparent to those ordinarily skilled in the art upon review of the following description of specific embodiments of the application in conjunction with the accompanying figures.

BRIEF DESCRIPTION OF THE DRAWINGS

Embodiments of the present application will now be described, by way of example only, with reference to the attached Figures, wherein:

FIGS. 3a and 3b show retinal images, obtained from color fundus imaging and wide field fundus imaging, in grayscale format;

DETAILED DESCRIPTION

Generally, the present application provides a method and system for quantifying disease progression through retinal health assessment and management.

Figure 1:
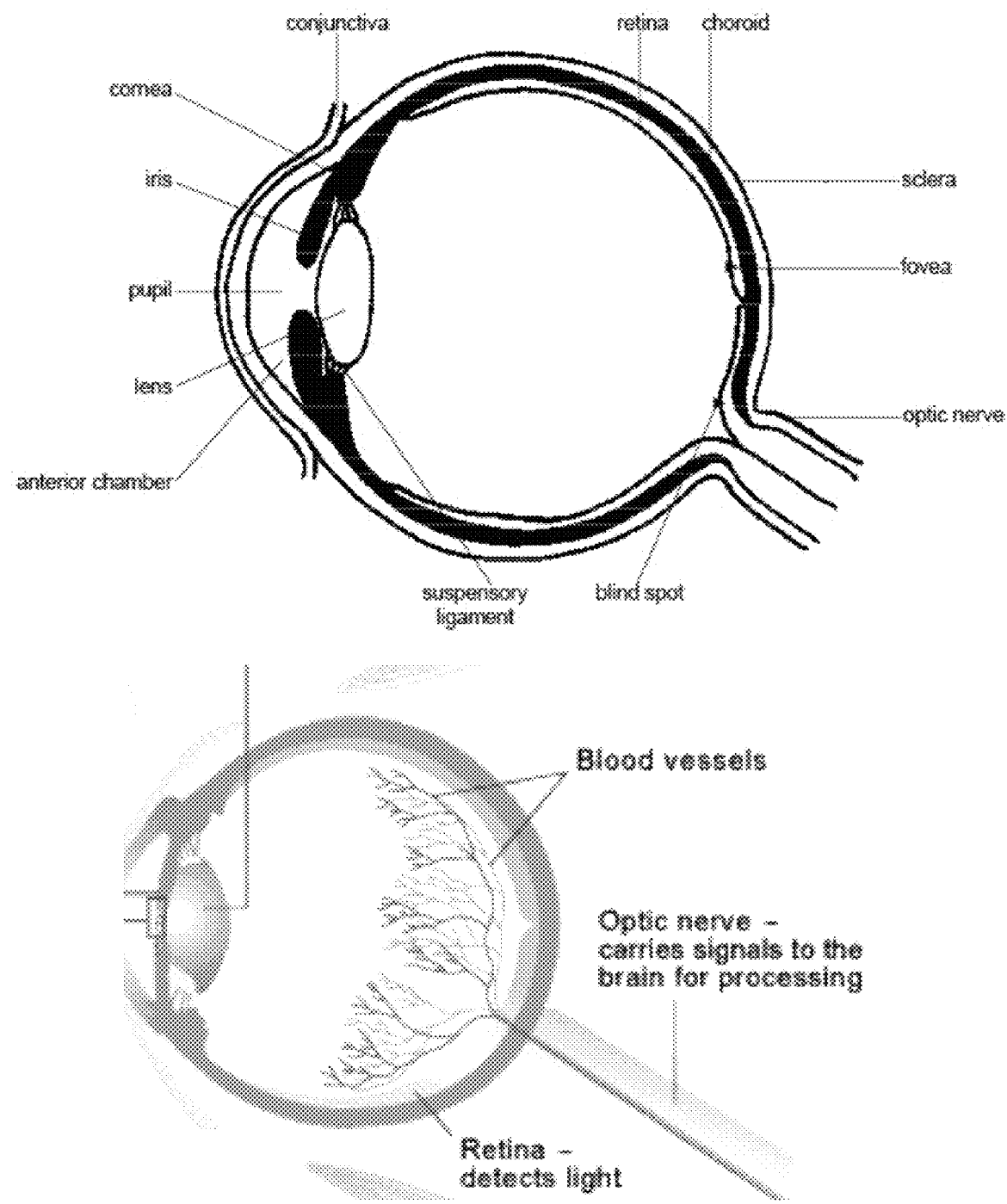
FIG. 1 is an illustration of the anatomy of the human eye.

The retina is located on a substantially spherical surface at the rear of the eye. The retina is layered as shown in FIG. 1. It contains not only the transducers (photoreceptors), i.e. light-sensing rods and cones, but also a vascular tree network of arteries and venules, all connected through the optical nerve head, cells responsible for maintaining a healthy environment for the retina and a neural network for information pre-processing.

The non-invasive retinal surveillance for ophthalmic purposes involves illumination of each region of the retina and the measurement of light reflected from it. A typical region of illumination is circular and corresponds to 45 degrees of visual field. In such an arrangement, the total retinal area of illumination would be about a square centimeter. Within this area, the spatial resolution of the viewing instrument may permit several million individual pixels to be measured. Moreover, the retina has a depth of about 0.25 mm, and certain types of measurement can preferentially select a certain depth of field, such that within one pixel, there may be many depth locations. In summary, non-invasive retinal measurements typically address many millions of retinal locations.

Compounding the amount of information associated with the millions of locations is the fact that each location can be characterized optically in many different ways. For example, the reflectivity of each region could be measured at a multiplicity of different wavelengths or spectral bands. The reflectivity could be analyzed in terms of its diffuse scattering and specular reflecting components. The reflectivity could also be characterized in terms of its polarization modifying properties. The reflectivity could be measured at different angles to generate a stereoscopic or 3D appearance. The location reflectivity could also be characterized by its dynamic response to illumination resulting from photochemical changes. The location could also be characterized by its fluorescence responses under different spectral conditions of excitation and collection.

Each type of measurement of each retinal location (pixel) will typically initially require the use of perhaps 12 bits of memory storage. Thus a full characterization of an eye may well require the use of many gigabits of memory. All this vast amount of information must be presented to the ophthalmologist in a way that most easily and effectively enables clinical information of significance to be discerned. Such information is determined primarily by the need to identify retinal pathologies and to monitor the rate of their progression over months or years.

Accordingly, there is provided a method to present images, in ways that enable and enhance the speed and reliability of diagnosis, to an ophthalmologist who then carries out the diagnosis.

Principal Diseases of the Retina

There are many diseases of the retina which can have a wide range of short or long-term impact on vision. The leading causes of catastrophic vision problems in the developed world are age-related macular degeneration (AMD or ARMD), diabetic retinopathy (DR or DRP) and glaucoma. These are chronic, degenerative conditions that can progress to legal blindness quickly (a few years) or slowly (several decades) depending on the patient. No cure exists for these diseases, but treatments do exist that can help slow progression, reduce vision loss and maintain some functional vision. The timing of most of these treatments is critical to optimize patient outcomes. Furthermore, it is generally agreed upon clinically that for these conditions, early detection of disease is crucial for mitigating the number and delaying catastrophic outcomes. For this reason, regular screening for these conditions and monitoring of disease progression is critical to eye disease management.

In an aspect of the present application, the method described herein can enhance eye clinicians' ability to objectively quantify progression and identify specific disease by utilizing the multi variable data plane. Information is intuitively presented in a retinal health management information package to enable better diagnosis and management of disease.

Disease Detection Today

Currently, retinal diseases are detected by an examination of the back of the eye via the optics of the eye (fundus exam or color image). This inspection can be performed using a number of optical tools available to eye care professionals. Because of cost and technical issues, only a few instruments are used in offices of the primary eye care professional. These are described below. In a fundus exam, white light illuminates the retina, and an image is obtained of the retinal structures from the light scattered from the mostly superficial tissues of the retina. The eye care provider looks for abnormal fundus features or changes in the fundus across several visits, which are indicators of disease. Disease detection can only occur once it has produced an anatomical change in the retina. In most conditions, the anatomical changes detected are irreversible and indicate an established progression of the disease.

Roles and Needs of Primary Eye-Care Providers

Primary eye care providers screen the population for retinal problems or risk of future retinal problems. They monitor the progression of any retinal condition before and after treatment and provide timely referral to retinal specialists (secondary and tertiary care) for diagnosis, treatment and follow-ups.

Each role is critical to ensuring optimized eye care when working with the rest of the ophthalmic care providers and requires technology whose outputs (Multi Spectral Data) can be packaged into novel way to enable several objectives identified here.

In the context of the retina, which does not include refractive errors, the primary eye care provider is concerned with 4 principal tasks that help drive the clinical decision process for a patient: (1) Identifying patients at risks of disease: the risk level will determine the protocol to monitor the possible onset of disease including types of tests and their frequency; (2) Identifying signs of disease onset/status: after the onset of a disease, the monitoring pattern will likely change depending on the progression pattern of the disease, this would include adding more tests and a consultation with a specialist to determine the nature of the disease and its development status; (3) Monitoring disease progression: after the disease has been identified, the primary eye care provider is often responsible for monitoring its progress until a critical point has been reached where there is a need for a specialist to get involved either for closer monitoring or treatment; and (4) Monitoring treatment efficacy: depending on the treatment and the disease, the specialist can often use a primary eye care provider, if the right tools are available in their clinic, to monitor treatment efficacy. The primary care provider is then responsible to refer back to the specialist to adjust treatment or if progression indicates a need.

Figure 2:
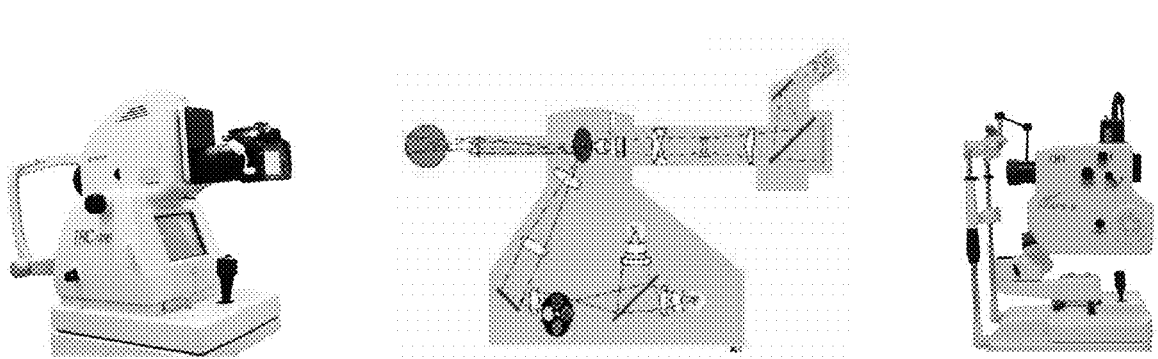
FIG. 2 shows instruments that are common in eye care practice.

To perform these tasks, the primary eye care providers require tools that can effectively probe the health of the retina. The instruments that are common in eye care practice are Opthalmoscope, color fundus camera, or scanning laser opthalmoscope, as shown in FIG. 2 and described below.

Opthalmoscope: An image of the patient's retinal anatomy is produced directly into the eye of the clinician, who then records what is seen in the patient's chart using notes and sketches. There are many optical designs to perform this task but the most prevalent is the binocular indirect opthalmoscope, BIO. The main advantage of the BIO is the ability to obtain a true 3 dimensional view of the retina, which improves greatly the ability to detect topographical changes on the retina. A further advantage of opthalmoscopes is the ability, by a skilled clinician, to scan the field of view across the whole retina (>200°) for a panoramic exam of the fundus. BIO provides small field of view ~5 degrees and requires examiner to slowly scan the eye. The patient exam takes several minutes, uses a very bright light; and requires that the patient's head be tilted back while the clinician observes the fundus. An opthalmoscope does not generate any record of the retinal image.

Color Funds imaging: When a permanent record is required, a camera is used to capture the fundus image. The camera projects the fundus image on a film plane instead of into the clinician's eye. The properties of fundus cameras vary greatly across manufacturers with differentiation parameters such as film/digital image planes, minimum pupil diameter, exposure times (sensitivity), light source, optical filters, field of view, software for managing patient information, etc. and many more.

In a fundus camera, the instrument alignment is performed by a technician (not the clinician) with moderate illumination and takes a few minutes. The fundus camera produces ~45 degrees field of view (FOV) color images, as illustrated in the greyscale image shown in FIG. 3a. Fundus image is typically obtained using a very bright flash (close to illumination limits of the eye) of a few milliseconds. The clinician can then observe the fundus image to present retinal health information to the patient.

Scanning opthalmoscope: This provides a simple fundus image. The image is obtained by raster scanning across the retina a focused laser beam. The 180 degree image is reconstructed from the raster scan in a computer, producing a digital record. Images are obtained with red and a green laser and are presented as a single view with both images superimposed, as illustrated in the greyscale image shown in FIG. 3b.

The purpose of any instrument currently available to the primary eye care provider is to provide a fundus image as discussed above, allowing the detection of anatomical changes of the retina resulting from disease.

In most retinal diseases, there can be time between the disease onset and the appearance of symptoms from patient vision loss or anatomical changes. In the retina the damage is usually the result of abnormal metabolic activity; part of the metabolism is abnormal and reduces the efficacy of some cells in the retina, usually the retinal pigment epithelium (RPE).

The internal system of a patient can compensate or tolerate the resulting "stress" to the retina but eventually there is a breakdown in some parts of the retina and anatomical changes start occurring at the cellular size. As a result anatomical changes build up over time and when enough changes have occurred these are detected in the BIO or color fundus image.

The ability to detect some changes in metabolic activity at the early stages of the disease provides the opportunity for much earlier detection of disease development. Mitigation of outcomes (delaying or eliminating catastrophic vision loss) depends critically on early detection of disease.

The Retinal Health Analyzer (RHA) system, in accordance with an embodiment of the present application, enables creation of metabolic data and anatomical imaging at different regions of the optical spectrum.

In addition to providing high quality and improved fundus imaging, the RHA provides the ability to quantify abnormal metabolic activity in the retina. Oxygen saturation and accumulation of cellular byproducts in the retina are key elements of metabolic activity.

All cells in the human body require oxygen to fuel the chemical reactions that produce cellular activity and the retina is the most metabolically active tissue in the body (more than brain or kidney). Disruption to cellular activity due to abnormal metabolism will automatically affect oxygen intake. Furthermore, oxygen is transported from blood vessels to the cells by diffusion. Consequently any disruption to the tissue will affect oxygen diffusion and thus metabolic activity. Monitoring oxygen saturation is a means of monitoring metabolic activity.

Oxygenation: The spectral signature of the scatter signal from blood is specific for the level of oxygenation contained in the blood. In the fovea only the choroid residing under all the retinal cells supplies oxygen for the retina. In other parts of the retina, there is substantial surface vasculature on top of the retina to supply the oxygen. The clinician will be able to select the appropriate retinal area for examination. The oxygenation map will be over a 45° FOV. By centering on the optic disk, an image of the oxygenation entering and leaving the optic nerve head (ONH) can be obtained and is considered important in Glaucoma. Similarly, by centering on the fovea, oxygen saturation in the critical macular region can be produced, which has been implicated in AMD and DR development.

All cells produce cellular waste during their activity and this waste must be broken down and disposed of through the vascular system to ensure good cellular function. Lipids are deposits of fats, and other metabolic by-products in the intercellular space, have been demonstrated to correlate to the development of retinal diseases. Although most people have some drusen, an increase of drusen numbers or size is a clear indicator of future visual problems. Because they reside deep in the retina, drusen can only be detected in fundus images after reaching a size that has already disrupted the retina. Drusens are detected via NIR imaging and through autofluorescence.

Risk of Missing the Disease

In the clinical decision process, the RHA measurements can have an impact as the clinician must decide if there is any suspicion of retinal problems now, or a risk of disease for the future.

The RHA provides previously unavailable information data for earlier and more reliable detection of disease or risk for disease because the clinician now has a whole arsenal of results to combine for making the clinical decision. This can reduce the risk of missing a disease.

The value added can be illustrated in this way: assuming that each tool has a 50% chance of detecting a small abnormality (this value is used for illustrative purposes only, real tests are much better), the random chance of missing the defects with two measurements is 0.50×0.50=0.25 or 25%. Adding a third measurement reduces the risk of missing the defect to 12.5% (0.5×0.5×0.5) and adding a fourth to 6.25%. In summary, the chance of four false negative results is much reduced.

Referral and Monitoring

After identifying a patient at risk of disease or exhibiting a clear sign of disease, the care provider must decide if the patient needs to be referred to a specialist. The RHA provides the clinician with objective quantification of retinal abnormality. Currently, all decisions are based on the subjective assessment of the fundus image by the clinician and referrals especially at the early stages of disease are hit and miss. This means that specialists that already have difficulty finding time to see all patients requiring their urgent care must also see many inappropriate referrals that simply get sent back to the primary care provider for monitoring until specialized care is required. On the reverse side, the primary care provider will now have objective measurements to base their referral decisions so that the optimal referral time for treatment, which optimizes the outcome, is not missed.

In many degenerative retinal conditions treatment can only occur at very specific time points of disease progression and it is critical to monitor progression closely so these trigger points for treatment are not missed. The new measurements provided by the RHA can help in establishing the optimal monitoring schedule and protocol for any patients, optimizing the clinical care relative to cost of testing for the patient.

Furthermore, when treatment is initiated, it is necessary to monitor treatment efficacy in order to adjust/modify treatment protocols. Because treatments do not reverse anatomical changes, fundus photography can only report that there is no progression in physical changes and this can take a long time to establish. The retinal metabolic activity monitoring provided by the RHA improves the clinician's ability to quantify the progress of a treatment earlier and objectively so that treatment can be optimized.

Information Created by RHA

The RHA acts like a light probe by capturing multispectral images at different depths in the retinal tissue. It can acquire a multiplicity of image data sets which may be at same or different wavelengths or spectral bands using any wavelength from ultraviolet to near infrared but typically ranging from 450 nm to 950 nm.

RHA provides images of the fundus obtained from 6 spectral bands from, for example, 470 nm to 950 nm. Data is used to enhance the detection of defects in different retinal tissue and enable detection of metabolic byproducts (for example: pigment, hemes, lipids, drusen). The selective spectral absorption of different tissues and the depth of penetration for different wavelengths of light make these spectral images powerful. For example, it is much easier for near-infrared (NIR) radiation to penetrate the full retina to the RPE than blue light. The vasculature of the retina dominates the color fundus image, which is why it appears red. By removing the red light one can enhance the image contrast of other non-vascular structures to identify any retinal abnormality. All multi-spectral retinal images cover ~45° FOV.

Images obtained from the RHA can be transformed into "pseudo-color" images for presentation to the clinician. The presented images are generated by applying an arithmetic function to corresponding pixel values of images captured at different spectral bands.

Images can be obtained from the RHA by capturing images with cross-polarized filters.

In an embodiment, a method for quantifying disease progression through retinal health assessment and management is provided. The method comprises obtaining a first image of a retina or iris at a point in time; generating a first vascular map of the first image of the retina or the iris; obtaining a second image of the retina or the iris at a later point in time; generating a second vascular map of the second image of the retina or the iris; registering the first image and the second image on the basis of the first vascular map and the second vascular map; and displaying at least one difference between the registered first image and the second image to quantify a disease progression. A registration method for multispectral retinal images (MSI) is disclosed in commonly owned U.S. Provisional Patent Application No. 61/297,475, filed on Jan. 22, 2010, which is incorporated herein in its entirety by reference.

After MSI data from different depths in the retina is collected by a high resolution camera, data is processed through an "intelligent Retinal Image Processing Pipeline" (iRIP2) allowing creation of metabolic maps, progression data graphs and image overlays. To improve clinician's ability to screen, identify, diagnose and monitor the disease a Clinical Viewer (CV) has been created. The multi-variable data is presented within 2D plane and allows improved data analysis during screening process and as well during disease management process. In the preferred embodiment data tabs and buttons are the means to switch among various viewing and data presentation modes in the Clinical Viewer.

The RHA provides the primary care physician with powerful tools that are not available in any other tools. The literature indicates that oxygenation, lipids, lipofuscin, and hemes have the potential to identify patients at risk of developing blinding eye diseases before any physical signs are available.

These measurements will provide quantitative methodologies for describing disease progression, a very significant improvement over the current qualitative methodology which are dependant on a clinician's pattern recognition capabilities.

The multi-spectral fundus imaging allows clinicians to better identify and quantify anatomical abnormalities, and their changes over time, by providing better contrast and deeper retina imaging.

The following table represents data tabs and buttons within the CV.

Figure 4:
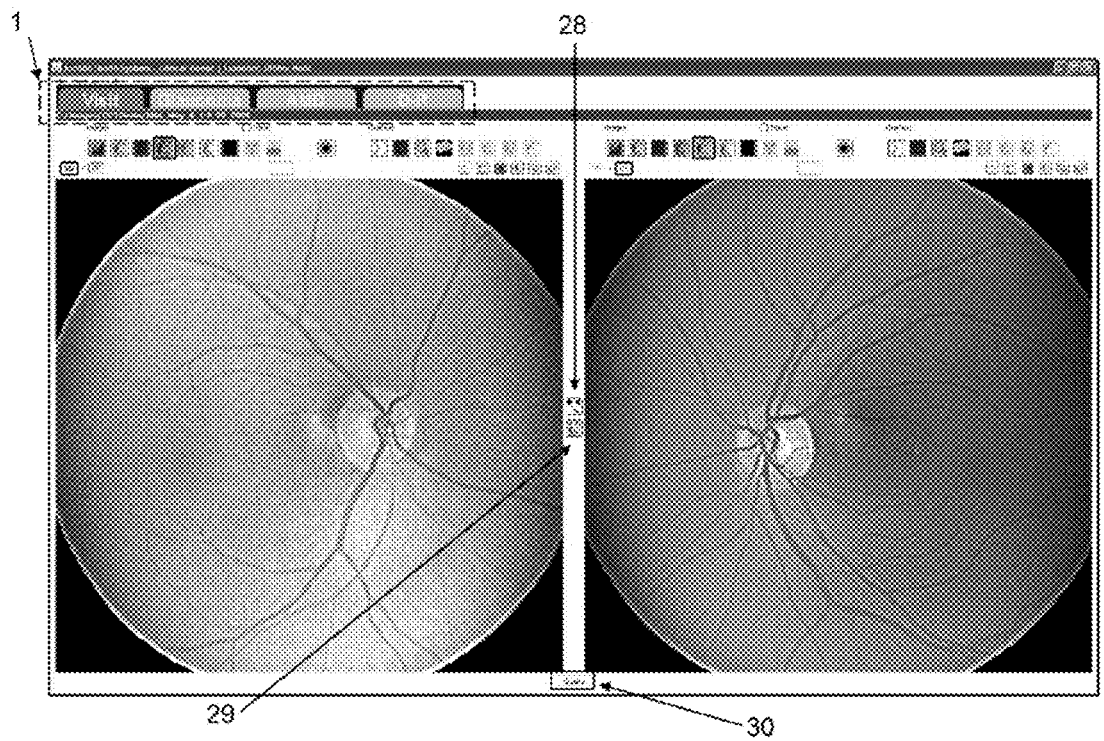
FIG. 4 is a graphical user interface of a clinical viewer in accordance with an embodiment.
Figure 5:
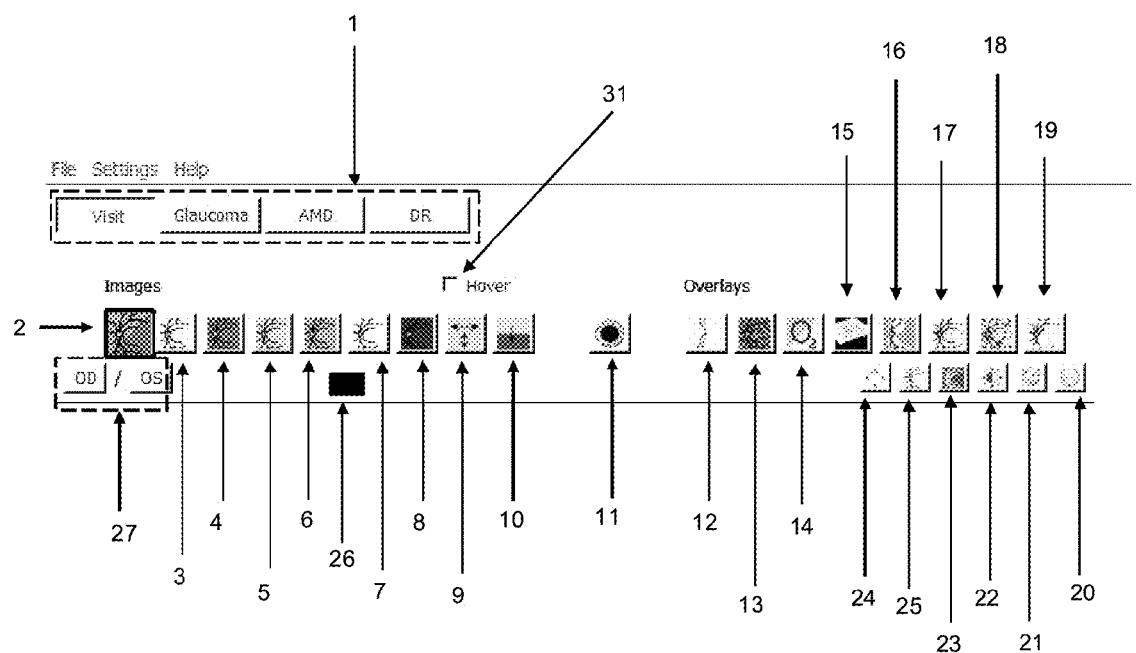
FIG. 5 shows, in more detail, the graphical user interface of the clinical viewer.

Clinical Viewer Button (GUI Menu, FIGS. 4 and 5) Descriptions:

1. Pathology tabs: Selects the display mode specific to a particular mode. For example: Visit (show everything) mode, glaucoma mode, age-related macular degeneration mode, and diabetic retinopathy mode
2. Display color image
3. Display wavelength 0 image (for example: infrared)
4. Display wavelength 1 image (for example: red)
5. Display wavelength 2 image (for example: amber)
6. Display wavelength 3 image (for example: green)
7. Display wavelength 4 image (for example: broadband green)
8. Display wavelength 5 image (for example: blue)
9. Display birefringence image
10. Display auto-fluorescence
11. Display the image of the iris
12. Enable the optic nerve head cup and disc ratio, and edit mode: quantitative information on C/D ratio, also trend analysis on progression of changes
13. Display the vessel map (track over time, identify new vessels grown in time)
14. Display the Oxygenation Map—Yellow Amber Ratio (YAR) image (relative oxygenation map in vessels and retinal tissue)
15. Display the stereo image (for example, anaglyph)
16. Display the retinal nerve fiber layer (RNFL) overlay
17. Display the drusen overlay: quantitative information on the number and size of drusens as well trend analysis of drusen will be produced (progression in % in coverage in specified region)
18. Display the blot overlay: quantitative information on the number and size of blots (hemes) as well trend analysis will be produced (progression in % in coverage in specified region)
19. Display the lipo overlay
20. Display metadata information about the current image
21. Refresh the image back to its original size and centre
22. Adjust contrast and brightness
23. Intelligent Image Visualization (I2V) —to allow enhanced view of wavelengths 0 to 5 (or to any other)
24. Overlay a 1 mm square grid for reference when approximating size
25. Display the image in full screen
26. Display calculated information based on the current mode or overlay
27. Select display of left or right eye (OD or OS)
28. Link the pan and zoom of both images. When depressed, panning or zooming on either image performs the corresponding movement on the other image. If the images are the same side (both OS or both OD), the panning moves in the same direction. If the images are different (one is OS and the other is OD) then side to side panning is reversed.
29. Link the two images' wavelengths. If the image is changed on one side, the same change is made to the other side.
30. Display the trend graphs.
31. Hover: When checked, it is not necessary to click the button change images—just mouse-over activates the button. This allows quick comparison of multiple wavelengths or spectral bands. (Optional, to roll the mouse button to allow changes)

Clinical Viewer

Figure 6:
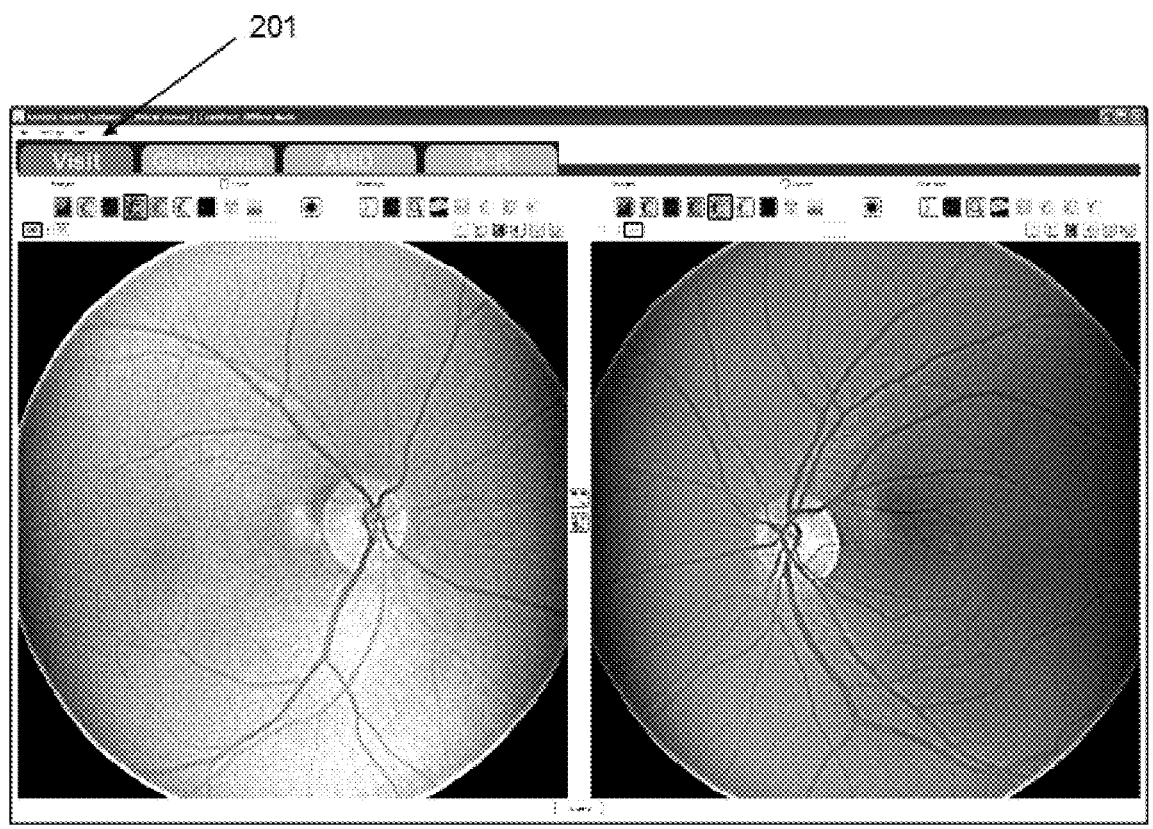
FIG. 6 is a graphical user interface of a visit screen of a clinical viewer in accordance with an embodiment.

The rich data sets allow data to be presented in a most efficient way within the CV. The CV has several tabs allowing General Visit 201 data (FIG. 6), and more selective and flexible data presentation which is useful for patients identified to be at risk, diagnosed or treated for specific eye disease of interest (AMD, DR, Glaucoma, Nevus, others . . . ). In the General Visit tab 201: MSI data (buttons 3 to 8)+Color Image (button 2) is presented in the general Visit view. It allows "at a glance view" of tissue health, by-products or potential pathologies at different depths of the retina. This general Visit view, allows clinicians to see two eyes (linked or not), if linked any function of viewing on OD eye will be reflected on OS eye.

By using "Hover" (button 31), one can easily move through the different spectral data sets by moving the mouse over button 2 to 8 without clicking on them. In addition, by selecting the hover button it is possible to roll the mouse and view the images in the image plane of the specific eye set without clicking, at the same time creating a sense of depth. This feature is enabled by utilizing the advanced registration of MSI data in space and time.

If the original data sets (tabs 3 to 8) reveal any specific area of interest and demand further investigation, the Processed Retinal Data tabs are available on the right side of the selected eye data sets. One can remain in the General view, and select buttons (9 to 20) to view oxygenation in the retina, drusen, vessel maps, stereo image, overlay meta data, Cup to Disc measurement, hemes, show trend maps for specific metabolite of interest or perform I2V.

In a disease management tab, clinicians can select any group of buttons (of processed data) to allow them to be in control of which information will most efficiently help them manage patients at risk or with specific eye disease.

For example, in the Glaucoma tab 301 (FIGS. 7-9): Enhanced ability to select data that is of interest for analysis of patients at risk from Glaucoma for example C/D, Stereo, I2V, oxygen in ONH, RNFL, C/D map over time 302.

Figure 10:
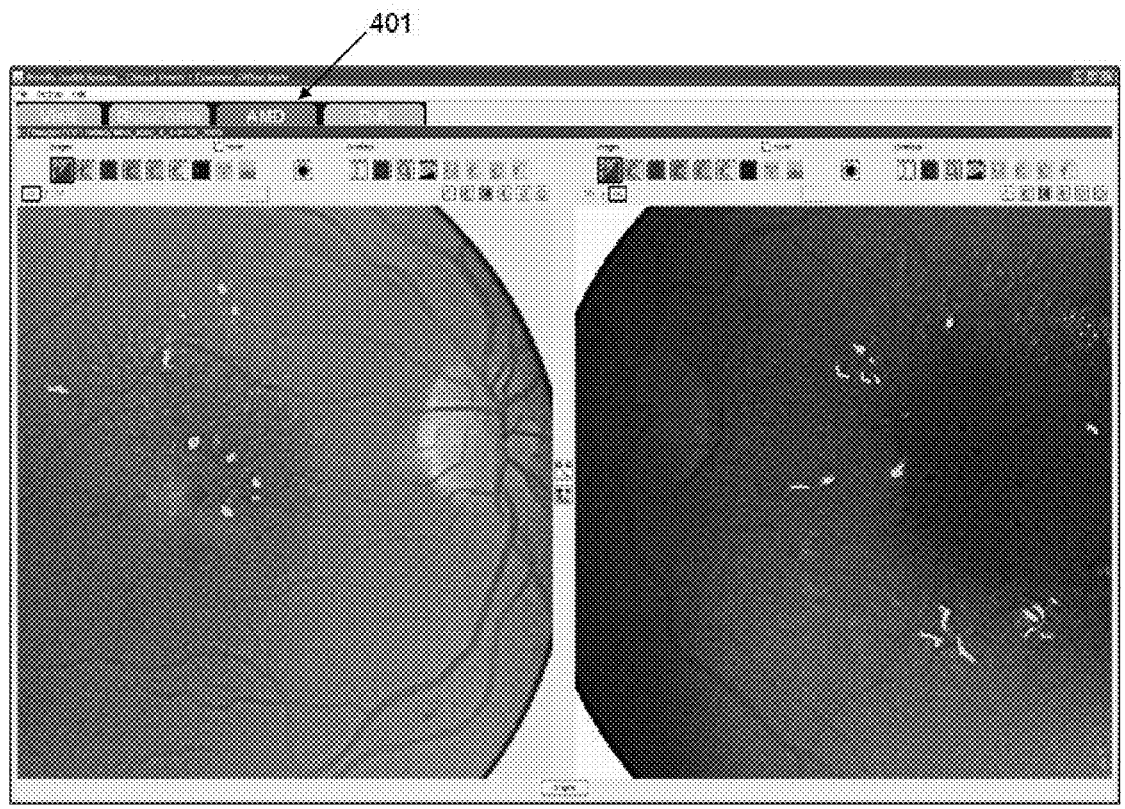
FIGS. 10-12 are graphical user interfaces of an Age Related Macular Degeneration (ARMD or AMD) management screen of a clinical viewer in accordance with an embodiment.
Figure 11:
Figure 12:
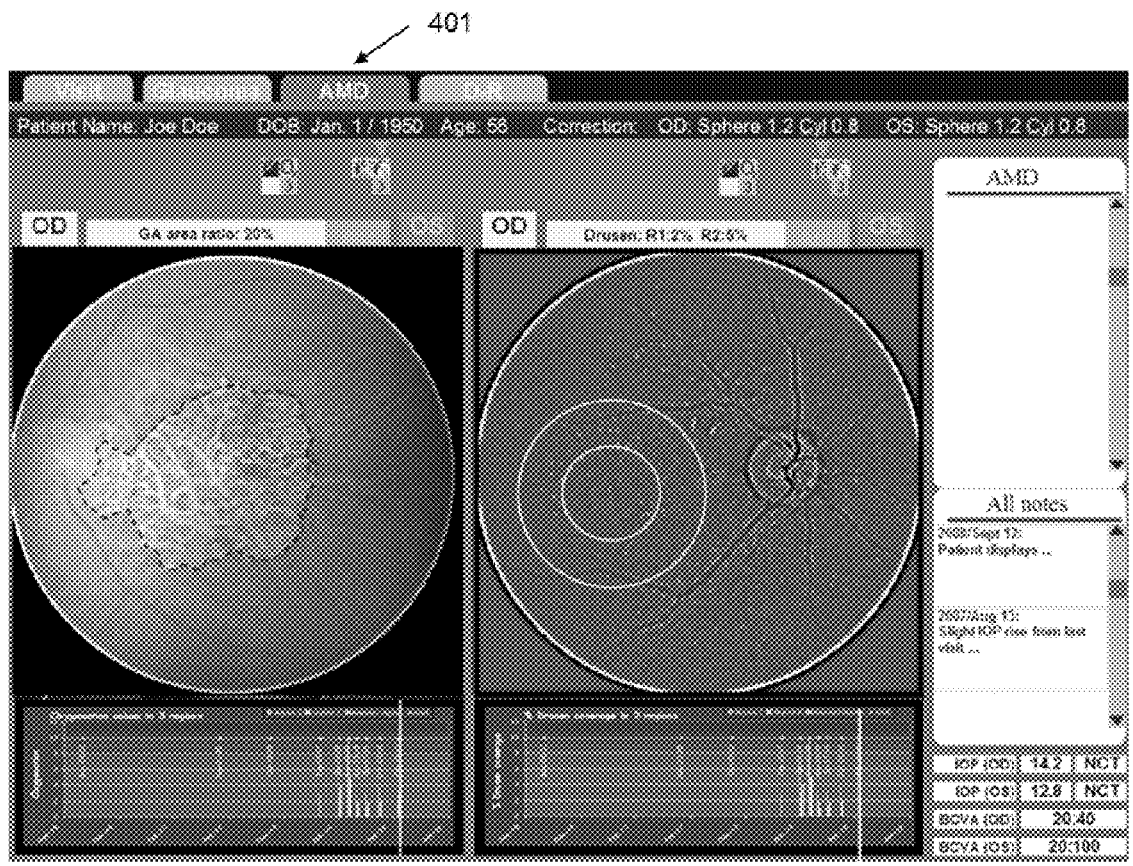

In the AMD tab 401 (FIGS. 10-12): Enhanced ability to select data that is of interest for analysis of patients at risk from AMD for example Oxygen map, Lipids map and trend graph over time 402, I2V for pigment, GA, Nivus and other byproduct enhancement; Color image, Lipofuscin, Stereo of macula.

Figure 13:
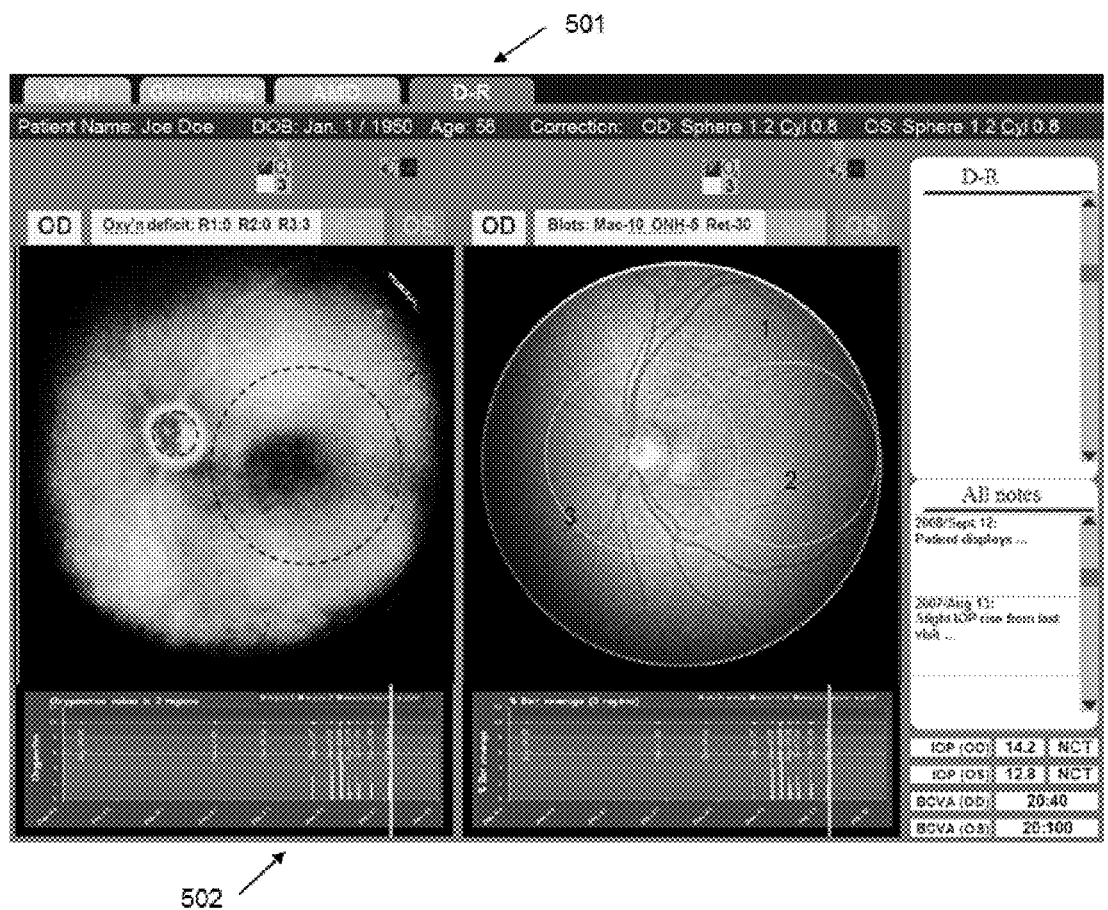
FIGS. 13 and 14 are graphical user interfaces of a Diabetic Retinopathy (DRP or DR) management of a clinical viewer in accordance with an embodiment.
Figure 14:
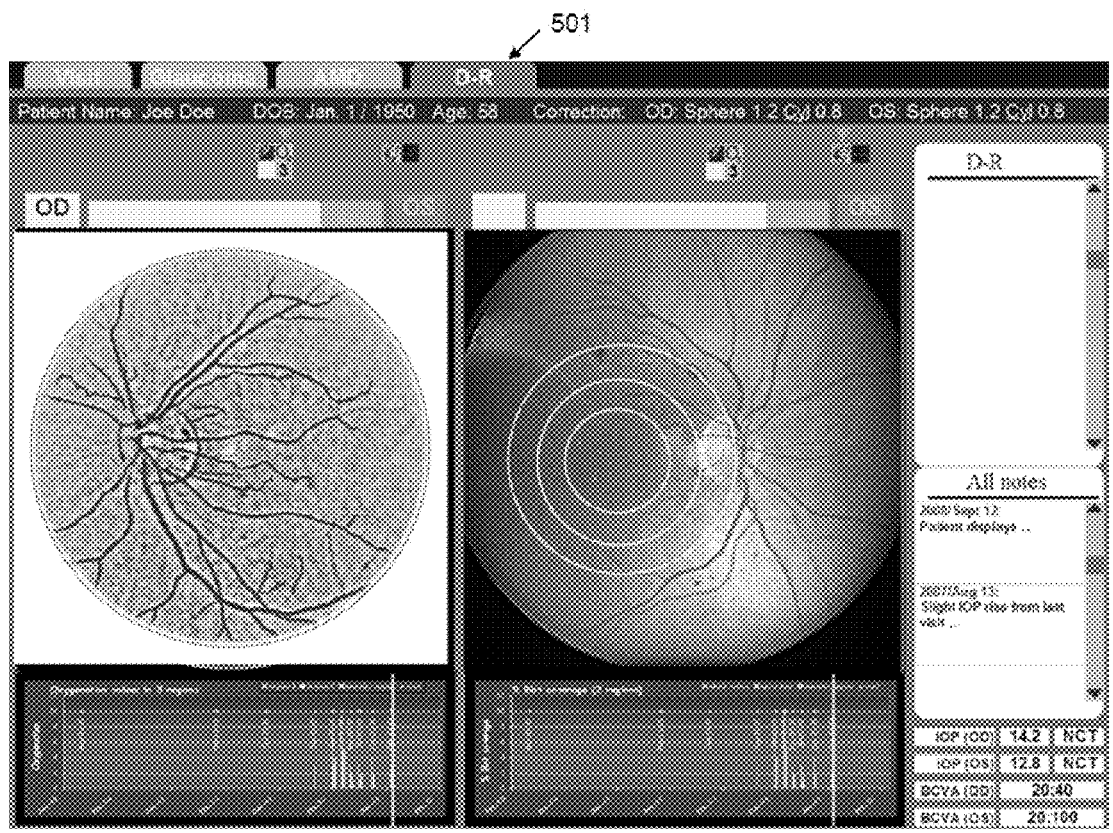

In the DRP (Diabetic Retinopathy) D-R tab 501 (FIGS. 13 and 14): Enhanced ability to select data that is of interest for analysis of patients at risk from DRP for example Oxygen map, hemes and trend graph over time 502, I2V for byproduct enhancement; color image, vessel map and delta map for showing progression.

Figure 15A:
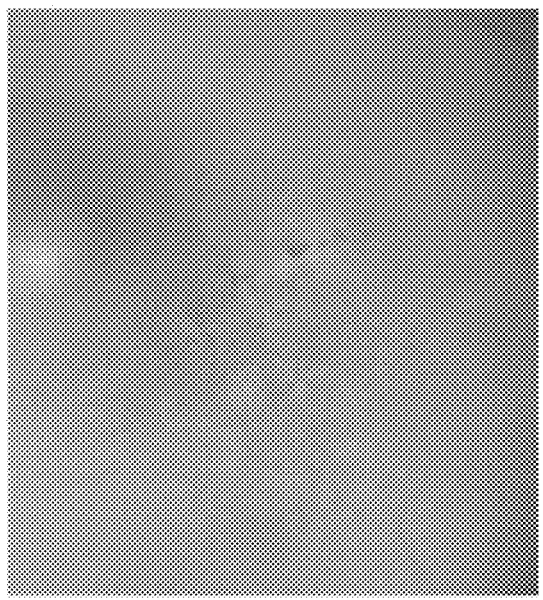
FIG. 15a shows an original retinal image and FIG. 15b shows a highlighted image identifying disruptions in the melanin cover.
Figure 15B:
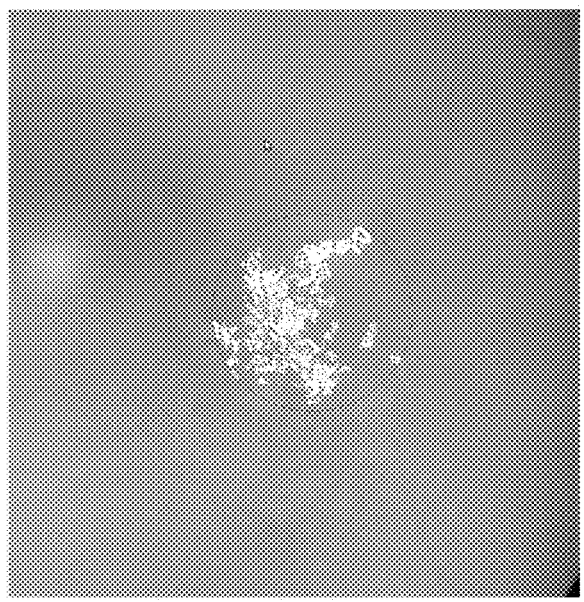

In a disease management tab according to one embodiment, a retina image, which can be generated using far red light (i.e. light having a wavelength between 700 and 800 nm), is searched for disruptions in the melanin cover of the macula. The melanin cover is expected to be dark when illuminated using far red light and any disruptions which are found are highlighted as high intensity spots in the melanin cover. FIG. 15*a* shows an original retinal image and FIG. 15*b* shows a highlighted image identifying disruptions in the melanin cover.

Clinical Value of Features and Data Provided

The measurements provided by the RHA and the presentation of data in the CV could have significant impact in the eye care practitioner office. The CV presentation could impact clinical decisions and the value added to the clinical exam by each measurement.

Another tool clinicians have traditionally used for treating glaucoma is the use of stereoscopic glasses to view inside and around the optic nerve cup. The clinical viewer provides a stereo view of the retina, and in particular, the optic nerve head. Dual pictures using stereoscopic glasses, combining the image using the anaglyph technique, and 3D modeling are all used to allow the clinician to have this view.

The Glaucoma View is an example of presenting specific relevant image data to complement the long term trend data. The combination of the two gives the eye clinician necessary diagnostic data in a connected fashion that they do not currently have.

For example, the clinician uses two key indicators for glaucoma detection and monitoring: Intra-ocular Pressure (IOP) and the ratio of various geometric parameters associated with the cup and disk regions of the optical nerve head. For example, the geometric parameter is the ratio between the surface area of the optic nerve cup and the surface area of the optic nerve disc (C/D ratio). In another example, the geometric parameter is the local deviation of the optical nerve cup from a smooth curve, in particular the local deviation is an outward deviation toward the rim, which deviation is called a "notch" and indicates thinning of the nerve layer outwards to the retina. In yet another example, the geometric parameter is the distance from the optical nerve cup edge to the optical nerve disc edge (the rim) in 4 directions, where the distances in a healthy eye are expected to follow the ISNT rule: the largest distance should be Inferior (down), followed by Superior (up), then Nasal (away from the macula), and the smallest distance is Temporal (toward the macula). In a further example, the geometric parameter is the ratio of the diameter of the cup in the horizontal direction to the diameter of the disc in the horizontal direction, or is the ratio of the diameter of the cup in the vertical direction to the diameter of the disc in the vertical direction. In particular, it is the change over time of these two indicators which provide the clinician with the necessary information for diagnosis.

Figure 7:
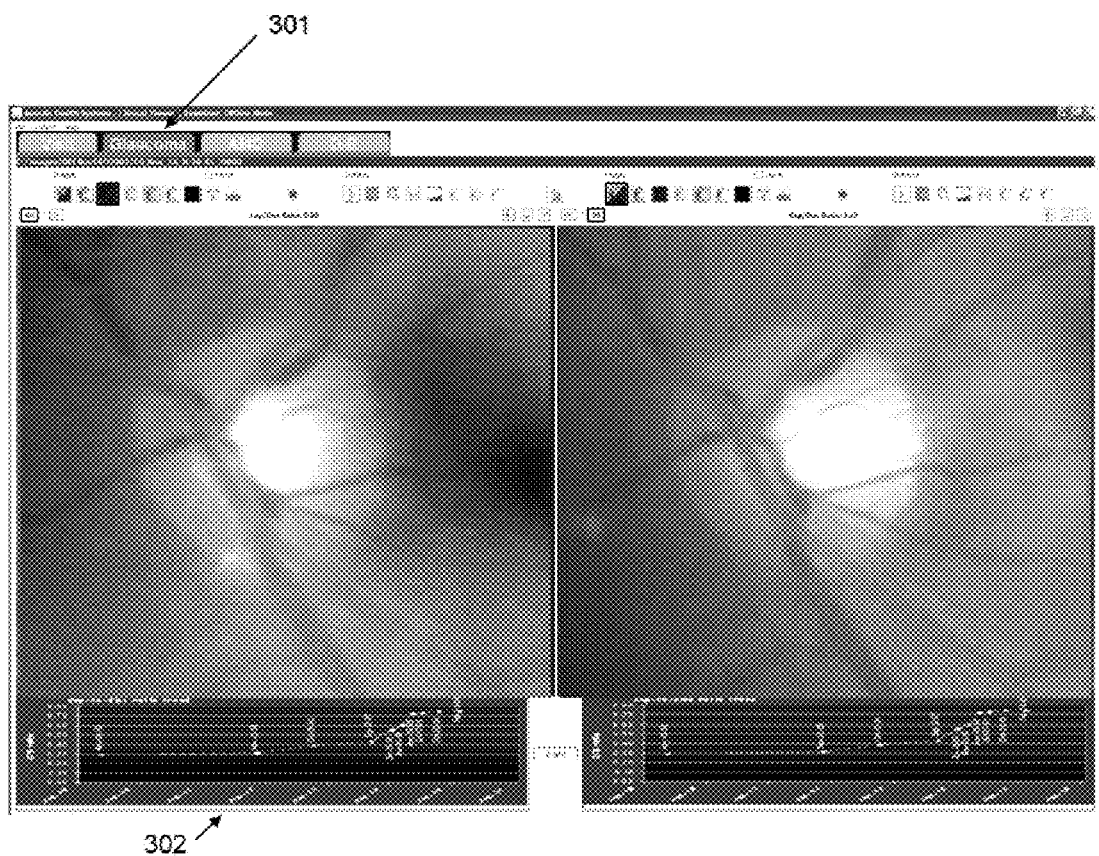
FIGS. 7-9 are graphical user interfaces of a Glaucoma management screen of a clinical viewer in accordance with an embodiment.
Figure 8:
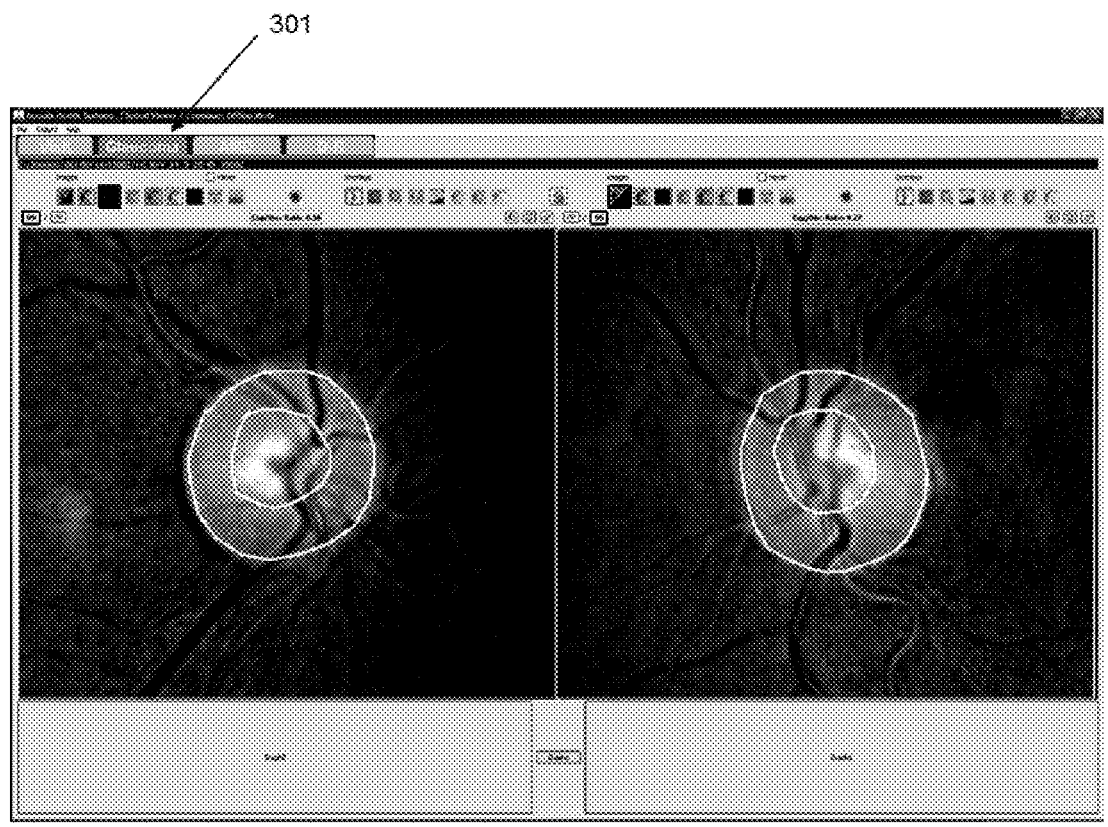
Figure 9:
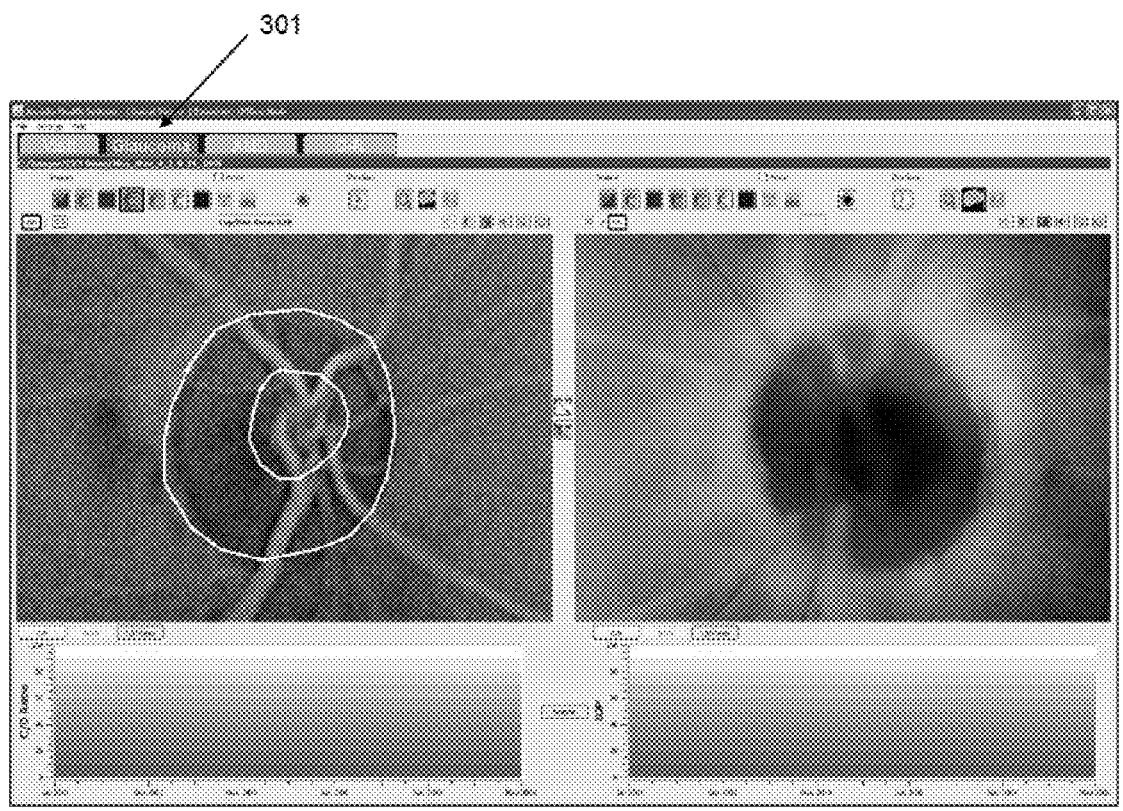

The Glaucoma View provides tracking information required with a single button click. Images for both eyes are displayed zoomed in on the optic nerve head with the outlines of the cup and disc overlaid graphically (as illustrated in FIG. 8). The image is enhanced to optimize the contrast of the optic nerve head (as illustrated in FIG. 9). Trend graphs 302 are displayed, with the patient's historic IOP measurements overlaid on the C/D ratios calculated from previous and current visits (as illustrated in FIG. 7). Further, editing tools are provided to refine the cup and disc measurements made by the image analysis software. All non-glaucoma-related information on the screen is hidden from view to allow the clinician to focus on the single disease.

Furthermore, summary reports can be printed for patient referrals to specialists or for the patient to take home for their records.

In summary, the following features are presented:

The screen presents simultaneously two retinal images, which can be used to identify differences and anomalies. The two images may be those of the left and right eyes. The images are generally retinal but may also be of the iris. They may alternatively be of the same eye but captured on different dates. They may alternatively show images that have been processed in different ways with the objective of enhancing the appearance of different disease characteristics (as illustrated in FIG. 7).

Such different processes include the ability to isolate a vascular map and superimpose it upon a map showing the selected diseases such as the presence of drusen, regions of low oxygenation, etc.

They may alternatively show the same eye captured from different perspectives, allowing the viewer access to a 3D stereo image when viewed with the aid of binocular glasses.

They may alternatively show the difference (delta) between images at different dates, comparing the changes in the left eye with those in the right eye.

The factors linking both images can be locked such that both images can be changed simultaneously in magnification, location, wavelengths, spectral bands, or any other determining measurement parameter or processing path.

Where left and right eyes are shown, the linking can be mirrored such that both optical nerve heads can be examined in detail together, or both macular regions.

All images may be magnified to focus more closely on areas of specific interest. In the case of glaucoma observation, the physician is assisted in creating contours that mark the perimeters of the cup and disk regions of the optical nerve head and generate automatically a ratio of geometric parameters which can be used for quantifying the severity of the disease.

Underneath the images, disease progression charts 302 (illustrated in FIG. 7) can be presented, giving instantly all the information most valuable for making treatment decisions. Measurement overlays are available to gauge the magnitude of diseased areas. All records can be annotated and previous annotations can be reviewed. The results may be printed. Extraneous information is removed whenever feasible to present as far as possible a simple, uncluttered presentation. All controls needed to generate images are located conveniently in a row at the top of the screen in iconic form.

Thus, a method and system for quantifying disease progression through retinal health assessment and management is provided.

In the preceding description, for purposes of explanation, numerous details are set forth in order to provide a thorough understanding of the embodiments of the application. However, it will be apparent to one skilled in the art that these specific details are not required in order to practice the application. For example, specific details are not provided as to whether the embodiments of the application described herein are implemented as a software routine, hardware circuit, firmware, or a combination thereof.

Embodiments of the application can be represented as a software product stored in a machine-readable medium (also referred to as a computer-readable medium, a processor-readable medium, or a computer usable medium having a computer-readable program code embodied therein). The machine-readable medium can be any suitable tangible medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the application. Those of ordinary skill in the art will appreciate that other instructions and operations necessary to implement the described application can also be stored on the machine-readable medium. Software running from the machine-readable medium can interface with circuitry to perform the described tasks.

The above-described embodiments of the application are intended to be examples only. Alterations, modifications and variations can be effected to the particular embodiments by those of skill in the art without departing from the scope of the application, which is defined solely by the claims appended hereto.

What is claimed is:

1. A method for quantifying disease progression through retinal health assessment and management comprising:
    obtaining a first image of a retina at a point in time;
    generating a first vascular map of the first image of the retina;
    obtaining a second image of the retina at a later point in time;
    generating a second vascular map of the second image of the retina;
    registering the first image and the second image on the basis of the first vascular map and the second vascular map;
    creating contours on the registered first image, on the second image, on the difference image, or on any combination thereof, that mark the perimeters of the cup and disk regions of the optical nerve head; and
    using a geometric parameter of the contours to quantify the progression of the disease, the geometric parameter being:
        the ratio between the surface area of the optic nerve cup and the surface area of the optic nerve disc;
        the local deviation of the optical nerve cup from a smooth curve;
        the distances from the optical nerve cup edge to the optical nerve disc edge in inferior, superior, nasal and temporal directions;
        the ratio of the diameter of the cup in the horizontal direction to the diameter of the disc in the horizontal direction; or
        the ratio of the diameter of the cup in the vertical direction to the diameter of the disc in the vertical direction.

2. The method according to claim 1, wherein the images are used to identify differences and anomalies in the retina.

3. The method according to claim 1, wherein the images are of the left and right eyes.

4. The method according to claim 1, wherein the images have been processed in a manner which enhances the appearance of a disease characteristic.

5. The method according to claim 4, wherein the enhancement process includes isolating the vascular map and superimposing the vascular map upon a map showing selected disease characteristics to enhance the disease characteristic.

6. The method according to claim 4, wherein the disease characteristic is the presence of drusen, regions of low oxygenation, pigment, hemes, lipids, or disruptions in the melanin cover.

7. The method according to claim 1, wherein the images are of the same eye captured from different perspectives, allowing a rendering of a 3D stereo image.

8. The method according to claim 1, wherein the images show a difference (delta) between images at different times, comparing changes in a left eye with changes in a right eye.

9. The method according to claim 1, wherein factors linking the images are locked such that the images are changed simultaneously in magnification, location, spectral bands, or any other determining measurement parameter or processing path.

10. The method according to claim 9, wherein, where left and right eyes are shown, the linking is mirrored such that both optical nerve heads, or both macular regions, are examined together.

11. The method according to claim 1, wherein the images are magnified to focus on areas of specific interest.

12. The method according to claim 1, wherein the local deviation is an outward deviation toward the rim.

13. The method according to claim 1, wherein the images are of the same eye and captured at different times, and the images show a difference over time.

14. The method according to claim 1, wherein the images are of the same eye captured at different spectral bands.

15. The method according to claim 1, wherein pixel values of the presented images are generated by applying an arithmetic function to corresponding pixel values of images captured at different spectral bands.

16. The method according to claim 1, wherein the images represent an auto-fluorescence of the retina.

17. The method according to claim 1, wherein the images are captured using cross-polarized filters.

18. The method according to claim 1, wherein the optic neuropathy is glaucoma.

* * * * *